United States Patent [19]
Williamson, IV et al.

[11] Patent Number: 5,452,837
[45] Date of Patent: Sep. 26, 1995

[54] SURGICAL STAPLER WITH TISSUE GRIPPING RIDGE

[75] Inventors: Warren P. Williamson, IV, Loveland; Leo J. Nolan, Cincinnati, both of Ohio

[73] Assignee: Ethicon Endo-Surgery, Inc., Cincinnati, Ohio

[21] Appl. No.: 349,706

[22] Filed: Dec. 5, 1994

Related U.S. Application Data

[63] Continuation of Ser. No. 184,804, Jan. 21, 1994, abandoned.

[51] Int. Cl.⁶ .................................................. A61B 17/068
[52] U.S. Cl. ............................................ 227/176; 227/19
[58] Field of Search ..................................... 227/175, 176, 227/180, 181, 19

[56] References Cited

U.S. PATENT DOCUMENTS

| | | | |
|---|---|---|---|
| 1,452,373 | 4/1923 | Gomez | 227/19 |
| 3,078,465 | 2/1963 | Bobrov | 227/19 |
| 3,079,606 | 3/1963 | Bobrov et al. | 227/19 |
| 3,315,863 | 4/1967 | O'Dea | 227/19 |
| 4,290,542 | 9/1981 | Fedotov et al. | 227/19 |
| 4,429,695 | 2/1984 | Green | 128/305 |
| 4,527,724 | 7/1985 | Chow et al. | 227/8 |
| 4,633,861 | 1/1987 | Chow et al. | 128/305 |
| 4,633,874 | 1/1987 | Chow et al. | 128/334 |
| 5,014,899 | 5/1991 | Presty et al. | 227/180 |

*Primary Examiner*—Scott A. Smith
*Attorney, Agent, or Firm*—Matthew S. Goodwin

[57] ABSTRACT

An improved surgical stapler is disclosed having a tissue gripping ridge on at least one of the tissue contacting surfaces. The tissue contact surfaces are preferably displayed on both the anvil and the cartridge surfaces of the surgical stapler. The tissue gripping ridges preferably have serrated surfaces which mesh when in contact with each other to hold the tissue.

The preferred embodiment of this invention describes the tissue gripping ridges along the periphery of the anvil and cartridge tissue contact surfaces. Another embodiment describes the tissue gripping ridges adjacent to the longitudinal knife slot.

6 Claims, 2 Drawing Sheets

SURGICAL STAPLER WITH TISSUE GRIPPING RIDGE

This is a continuation of application Ser. No. 08/184,804, filed Jan. 21, 1994 now abandoned.

BACKGROUND OF THE INVENTION

This invention relates to an instrument for applying surgical staples to body tissue. More particularly, the invention relates to a surgical stapler which has been adapted to more easily grip tissue between the tissue contacting surfaces of the instrument.

There is an increasing use of surgical stapling instruments to suture body tissue such as intestine, lung, stomach, and esophagus. Stapling tissue in most instances produces less scar tissue formation, requires less time and simplifies previously difficult surgical procedures when compared with traditional suturing methods. Surgical staplers of the type used in these procedures function generally by clamping the tissue between two opposed jaw components of the instrument. After the tissue is squeezed to a desired thickness, staples are fired through the tissue causing intimate contact of the tissue layers. Proper healing of tissue requires such contact, along with adequate blood supply.

Typically, the opposed jaw components of surgical staplers used to fasten layers of body tissue are a cartridge or staple holding jaw and an anvil or staple forming jaw. Such stapling devices are typically designed to apply multiple parallel rows of staples. Some staplers provide pairs of staple rows with a movable knife between the row pairs. The knife is important when tissue is required to be separated.

Mechanisms for clamping the tissue by closing the jaw components and forming the staple are typically included in such surgical staplers. U.S. Pat. No. 4,527,724, shows a linear stapler having an anvil jaw and a staple holding jaw. This type of stapler forms at least two parallel rows of staples but has no knife. The tissue clamping and staple forming functions are performed remotely from the tissue contact end of the device. U.S. Pat. Nos. 4,429,695, 4,633,861, and 4,633,874 show other linear stapler variations, each having an anvil jaw and staple holding jaw component in addition to a movable tissue cutting knife.

In order to produce the most desirable result in a surgical stapling procedure, the staples must be placed in the exact location desired by the surgeon and the resulting cut edge of tissue retain adequate blood supply for healing after stapling. The surgeon selects the precise location for the staple line, then places the opposed jaws over the tissue at that location and clamps the jaws together prior to firing the staples and cutting the tissue. Body tissue is usually kept moist on the surface during the surgical procedure and tends to slip out of the clamped jaws. Most surgical staplers utilize a pin to help align the jaw components for better staple formation, but the pin also tends to hold the tissue in place during the stapling procedure. The pin, however, holds tissue at one location only, requiring the jaw component surfaces to hold the remaining line of tissue layers in proper position. U.S. Pat. No. 5,014,899 shows a spring loaded button which is intended to hold tissue at one location between the jaws of a surgical stapler. Unfortunately, the net effect of these mechanisms to hold the tissue are that the tissue layers to be stapled can slip between the jaw components resulting in an irregular staple line and cut edge. This result can require the stapling procedure to be repeated which may not be possible because of lack of usable remaining tissue.

Not only is it desirable to hold the clamped tissue layers in the chosen position, but also to allow adequate blood supply at the cut edge. If inadequate blood supply occurs, healing either does not take place or is very slow. Selection of the final jaw closing gap value is a major factor in tissue healing after stapling.

One method of increasing the blood supply at the staple line is to compress the tissue to such an extent that crushing or bruising of body tissue occurs. The jaw closing gap value can be selected to cause tissue crushing which will occur over the entire tissue contact surface of the jaw components. This choice can also result in a staple height which is too small and will cause necrosis of tissue around the staples after the jaws are opened because the blood supply is restricted by the small staple height.

Accordingly, in view of the tissue clamping deficiencies in current surgical linear staplers, what is needed is a better way to hold clamped tissue in its chosen position until completion of the stapling and cutting procedure. In addition to the better way of holding clamped tissue, a better tissue healing condition is desirable by restricting the area to be crushed, thereby increasing the blood supply to the desired level.

SUMMARY OF THE INVENTION

The present invention is an improvement to the conventional surgical stapling instrument. The conventional surgical stapling instrument generally has opposed jaw components, one containing a cartridge having a plurality of slots for carrying surgical staples, and the other having an anvil for forming the staples. The cartridge has a tissue contacting surface and the anvil has a staple forming surface. The jaw components are movable toward each other for the purpose of gripping body tissue to the desired thickness between the tissue contacting and staple forming surfaces before forming the staples through the tissue. The conventional surgical stapling instrument usually contains a longitudinal knife slot in the jaw components to accommodate a moving tissue cutting knife.

The improvement to the conventional surgical stapler to which this invention specifically relates comprises a tissue gripping ridge displayed on either or both of the tissue contacting surfaces of the jaw components. This ridge causes better clamping of tissue between the jaw components and better healing of the stapled and cut tissue. The tissue gripping ridge preferably extends the entire length of the longitudinal axis of the staple holding or staple forming surface of the jaw components. The ridge preferably has a serrated surface, and when both jaw components display a ridge with serrated surfaces, the ridges are ideally located so that the serrations on the ridge surfaces mesh with each other when the jaw components are moved into contact with one another.

The preferred embodiment of this invention has the tissue gripping ridge displayed along the perimeter of the tissue contacting surface and the staple forming surface.

In another embodiment of this invention, the cartridge has one tissue gripping ridge displayed adjacent to one side of the longitudinal knife slot and the other ridge displayed on the other side of the knife slot.

The improved stapler of this invention can be used in any surgical procedure where it is desirable to fasten bodily tissue. It can also be used in not only conventional open procedures, but also endoscopic surgical procedures.

BRIEF DESCRIPTION OF THE DRAWINGS

An embodiment of the invention is described by way of example with reference to the accompanying drawings, in which.

DETAILED DESCRIPTION OF THE PREFERRED EMBODIMENT

Figure 1:
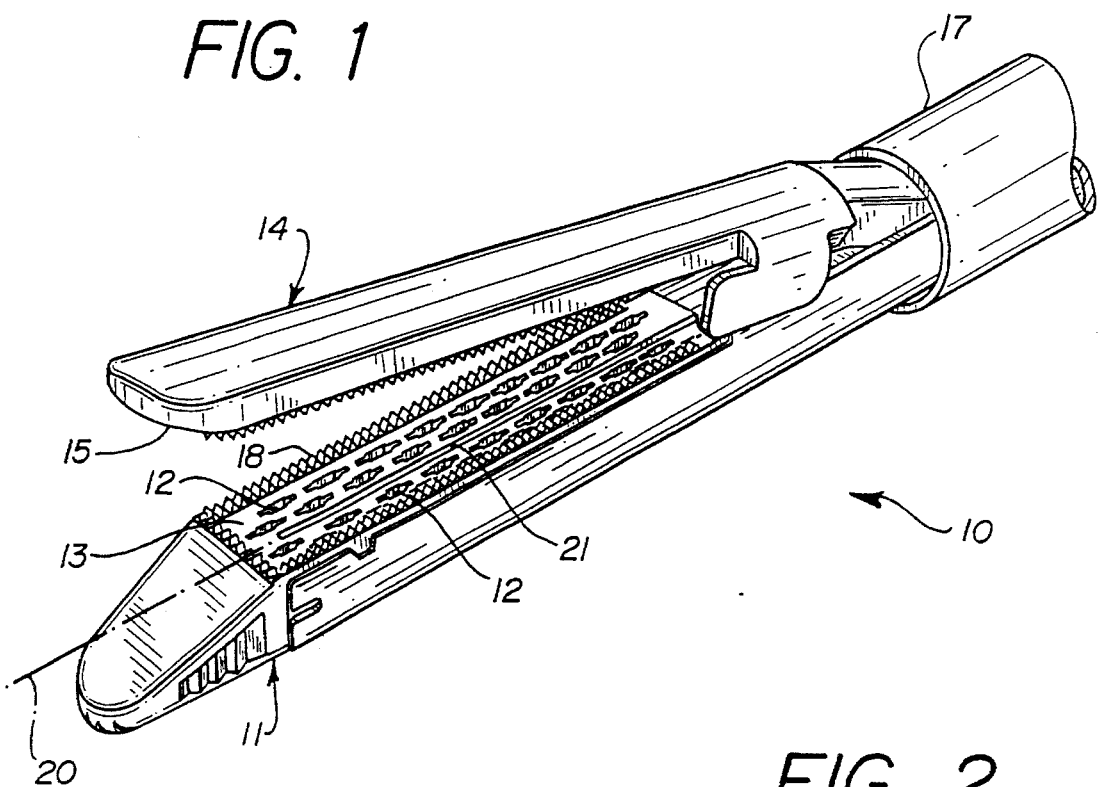
FIG. 1 is a perspective view of the surgical stapler as seen from the top and right side.

Referring now to FIG. 1, there is shown the preferred embodiment of the improved surgical stapler 10. It has a cartridge 11 containing a plurality of slots 12 which carry the surgical staples (not shown). The slots are arranged in two offset, double rows. The cartridge 11 has a tissue contacting surface 13. The stapler 10 also has an anvil 14 for forming the staples. The anvil 14 has a staple forming surface 15. The anvil 14 and cartridge 11 generally move toward each other to squeeze body tissue layers 16 before stapling them together.

Figure 2:
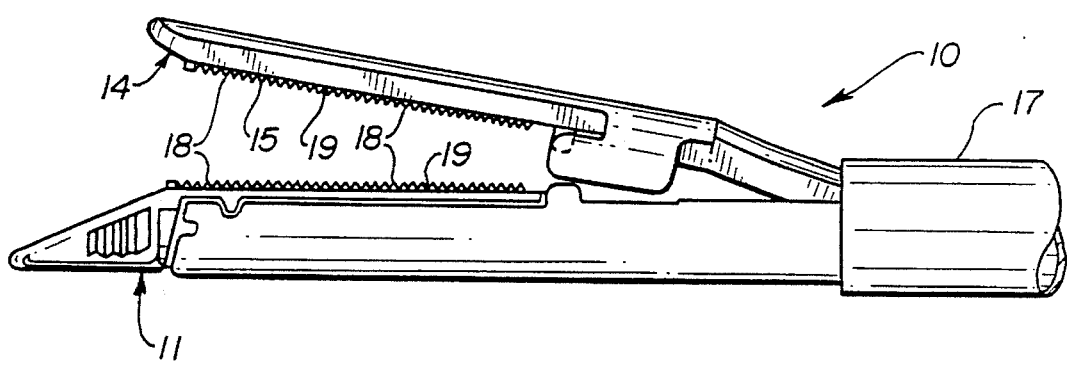
FIG. 2 is a side elevation view of the surgical stapler as seen in the open position.
Figure 3:
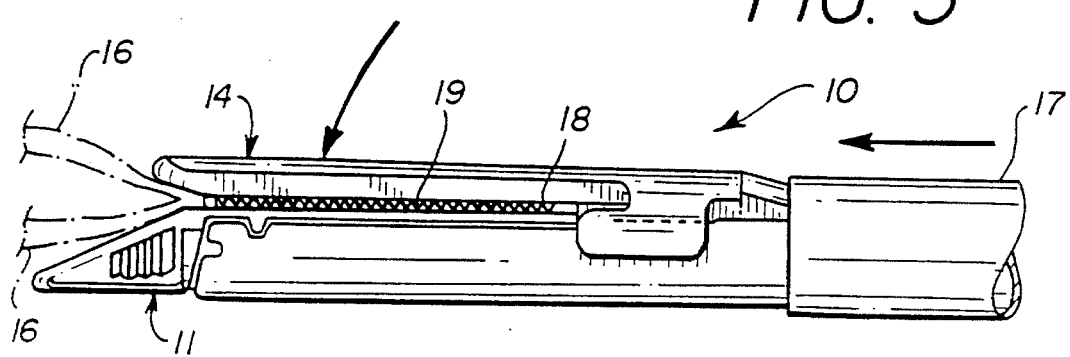
FIG. 3 is a side elevational view of the surgical stapler as seen in the closed position.

FIGS. 2 and 3 show the stapler 10 in its open and closed positions. FIG. 3 shows body tissue 16 clamped between the cartridge 11 and anvil 14. The closing motion can be accomplished in several ways. FIGS. 1–3 show a method using a cylindrical tube 17. The distal motion of the tube 17 will force the anvil 14 to close against the cartridge 11. This closed position is shown on FIG. 3. To open the stapler, the tube 17 is moved away from the end of the stapler 10, which allows the cartridge 11 and anvil 14 to rotate away from each other. This open position is shown in FIGS. 1 and 2.

In order to grip the tissue 16 to be stapled, both the cartridge 11 and anvil 14 have tissue gripping ridges 18. The tissue gripping ridges have serrated surfaces 19. The serrations 19 on the tissue gripping ridges 18 mesh when the ridges 18 are brought together. The meshing feature is shown on FIG. 3. In the preferred embodiment shown on FIG. 1, the tissue gripping ridges 18 are placed along the periphery of both the cartridge 11 and anvil 14. Also, the ridges 18 are parallel to the longitudinal axis 20 of the stapler 10.

Figure 4:
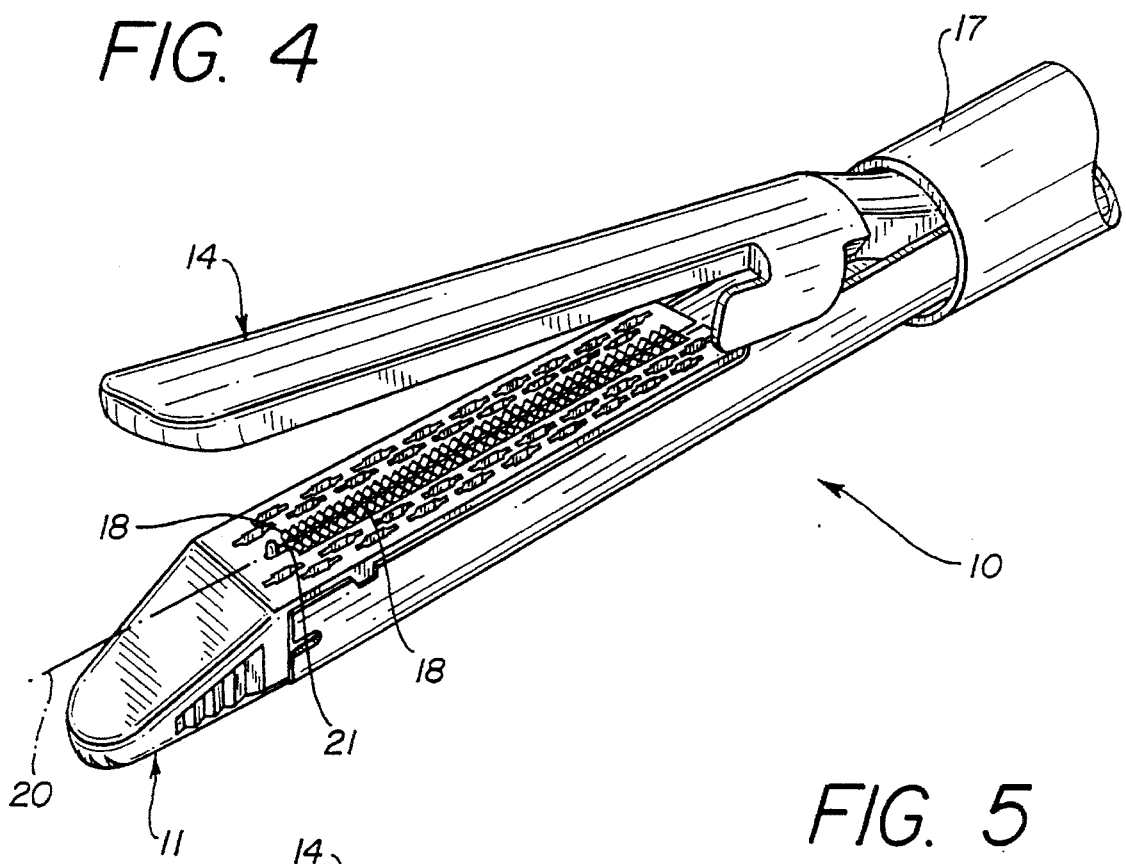
FIG. 4 is a perspective view of an alternate embodiment of the surgical stapler as seen from the top and right side.
Figure 5:
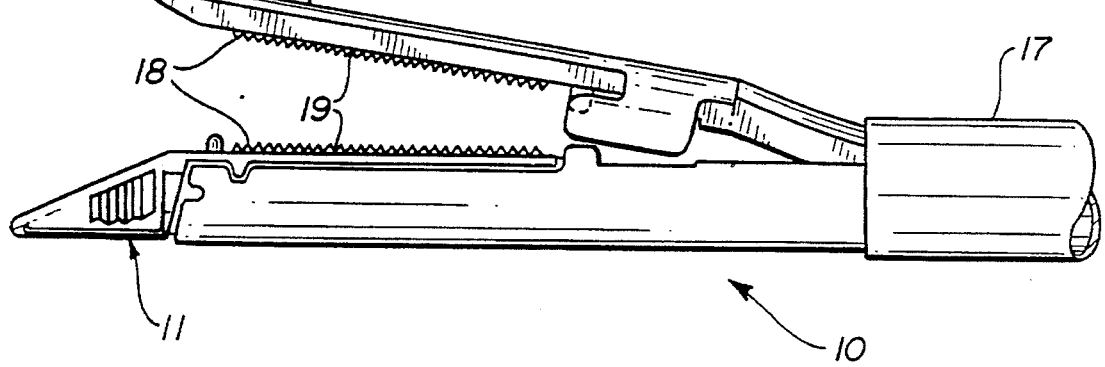
FIG. 5 is a side elevational view of the surgical stapler of FIG. 4 as seen in the open position.
Figure 6:
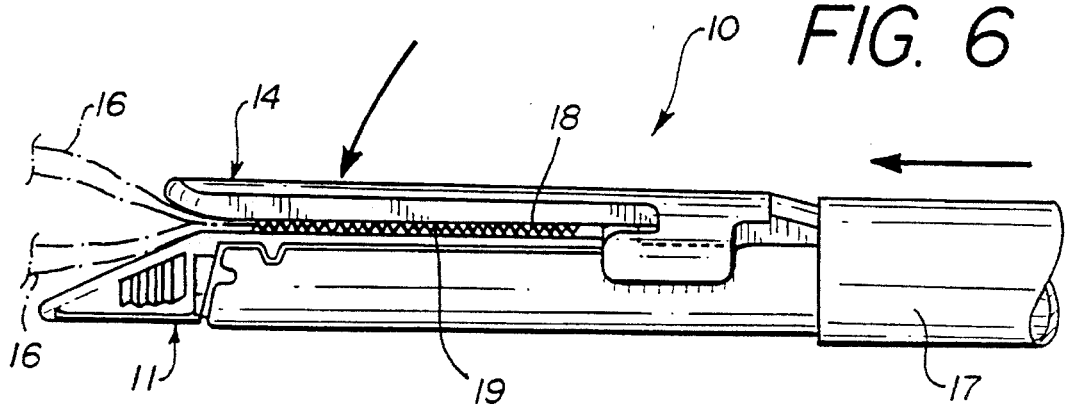
FIG. 6 is a side elevational view of the surgical stapler of FIG. 4 as seen in the closed position.

Another embodiment of this invention is shown on FIGS. 4 through 6. In this embodiment, the tissue gripping ridges 18 are placed in a different location. Many surgical staplers have a longitudinal knife slot 21 dividing the double rows of slots, as shown in FIGS. 1 and 5. This embodiment applies to the same stapler 10 configuration having a cartridge 11 and anvil 14. The cartridge 11 and anvil 14 are caused to move in the same manner, typically using a closing tube 17. This opening and closing function is shown on FIGS. 5 and 6 in the same manner as shown on FIGS. 2 and 3. The tissue gripping ridges 18 are located adjacent to the knife slot 21 in this embodiment. The knife slot 21 is along the longitudinal axis 20 and tissue gripping ridges 18 are parallel to the longitudinal axis 20. The anvil 14 also has a longitudinal knife slot (not shown) which is the same as the cartridge knife slot. The tissue griping ridges 18 on the anvil 14 are also located adjacent to the knife slot and are parallel to it. The serrated edges 19 of the tissue gripping ridges 18 mesh and squeeze tissue 16 in the manner shown on FIG. 6.

This invention is described with respect to its most preferred embodiments. However, the reader should realize that numerous additional embodiments are contemplated within the scope of this invention as it is defined by the appended claims.

What is claimed is:

1. An improved surgical stapler of the type having a cartridge containing a plurality of slots for carrying surgical staples, said cartridge having a tissue contacting surface thereon, and an anvil for forming said staples, said anvil having a staple forming surface thereon facing said tissue contacting surface, each of said tissue contacting surface and said staple forming surface having a perimeter defined by an external peripheral boundary bordering each of said surfaces, at least one of said anvil and said cartridge being movable toward the other for gripping bodily tissue therebetween; the improvement wherein tissue gripping ridges are displayed substantially along said perimeter of each of said tissue contacting surface of said cartridge and said staple forming surface of said anvil, said tissue contacting surface and said staple forming surface each have a longitudinal axis, and said tissue gripping ridges extend parallel to said longitudinal axis of each of said tissue contacting surface and said staple forming surface for a portion thereof, and transversely to said axes at a distal end of said tissue contacting surface and said staple forming surface for a portion thereof.

2. The stapler of claim 1 wherein said tissue gripping ridges extend the entire length of each of said tissue contacting surface and said staple forming surface.

3. The stapler of claim 2 wherein said tissue gripping ridges have serrated surfaces.

4. The stapler of claim 3 wherein said tissue gripping ridge of said tissue contacting surface is opposed to said tissue gripping ridge of said staple forming surface.

5. The stapler of claim 4 wherein said opposed serrated surfaces of said tissue gripping ridges on said tissue contacting surface and said staple forming surface indirectly mesh when tissue is gripped therebetween.

6. The stapler of claim 5 wherein said cartridge has two offset double rows of said slots, said double rows divided by a longitudinal knife slot.

* * * * *